United States Patent [19]

Min et al.

[11] Patent Number: 5,399,700
[45] Date of Patent: Mar. 21, 1995

[54] METHOD FOR PREPARING ENTERIC-COATED ORAL DRUGS CONTAINING ACID-UNSTABLE COMPOUNDS

[75] Inventors: Dong S. Min, Seoul; Kee A. Um; Yong S. Kim, both of Suwon; Pyong W. Park, Seoul, all of Rep. of Korea

[73] Assignee: Sunkyong Industries Co., Ltd., Suwon, Rep. of Korea

[21] Appl. No.: 997,791

[22] Filed: Dec. 29, 1992

[30] Foreign Application Priority Data

Dec. 31, 1991 [KR] Rep. of Korea ............... 91-25847

[51] Int. Cl.$^6$ ........................................ C07D 401/12
[52] U.S. Cl. ........................................ 546/271
[58] Field of Search ............................ 546/271

[56] References Cited

PUBLICATIONS

Organic Chemistry. Morrison and Boyd. Allyn and Bacon Inc. Boston. 1966. p. 520.
Senn–Bilfinger et al. CA 104:188579P and CA 104:188580g 1986.

Primary Examiner—Jane T. Fan
Attorney, Agent, or Firm—Kenyon & Kenyon

[57] ABSTRACT

The present invention relates to a method for preparing enteric-coated oral drugs containing acid-unstable compound, in particular an enteric-coated oral drug prepared in the form of acid-stable dosage units as inclusion complex formed by reacting benzimidazole derivative, acid-unstable compound, with cyclodextrin in alkaline solution.

12 Claims, No Drawings

METHOD FOR PREPARING ENTERIC-COATED ORAL DRUGS CONTAINING ACID-UNSTABLE COMPOUNDS

BACKGROUND OF THE INVENTION

The present invention relates to a method for preparing enteric-coated oral drugs containing acid-unstable compounds, in particular an enteric-coated oral drug prepared in the form of acid-stable dosage units as inclusion complex formed by reacting benzimidazole derivative, acid-unstable compound, with cyclodextrin in alkaline solution.

Acid-unstable compounds, especially the benzimidazole compounds, are easily discolored and degraded under acidic and neutral conditions. For example, omeprazole, a benzimidazole derivative, has half-life of 10 minutes in medium of below pH 4, but 18 hours at pH 6.8 and about 300 days at pH 11. Omeprazole has been reported to be stable in alkaline condition [Pilbrant A and Cederberg C. Scand. J. Gastroenterology, Suppl. 108, 113-120(1985)]. The acid-unstable compounds when exposed to the environment also get discolored and degraded by getting in contact with moisture and organic solvents.

Therapeutic use of the acid-unstable compounds which inhibit gastric acid secretion and are used to cure peptic ulcer and/or duodenal ulcer, requires appreprate mechanism to protect these compounds from degradation in gastric juice after oral administration.

Methods for stabilizing the acid-unstable compound, in particular omeprazole has been known to be as follows; Omeprazole is combined with alkaline salt such as $Na^+$, $K^+$, $Mg^{+2}$, $Ca^{+2}$ and so on to maintain the stability for compound itself. PCT Publication No. 86-00913(PCT/EP 85/00371) discloses to form a stable complex by mixing and reacting omeprazole with $\beta$-cyclodextrin in 96% ethanol and cooling the reactant.

The latter process seems to have the problem as the reaction is conducted at a temperature $25° \sim 38°$ C. for 15 hours in ethanol, during the reaction itself omeprazole can get discolored and degraded. Furthermore, it is difficult to expect the formation of inclusion compound because both omeprazole and cyclodextrin are dispersed in the reaction as solid particles, not dissolved. For forming an inclusion compound of cyclodextrin, the reaction must be carried out in presence of water molecules [K. Hara, H. Hashimoto, J. Jpn. Soc. Starch. Sci., 32(2) 152-161(1986)]. Therefore, the latter method not expected to give inclusion compound since the above reacting condition has not been considered.

On the other hand, Unexamined Korean Patent No. 87-9718 and Korean Patent Publication No. 91-4579 disclose processes for preparing omeprazole preparation consisting of mixing omeprazole with alkaline substance to form core material, forming a watersoluble internal layer on the core and forming an enteric coating to stabilize omeprazole.

It has, however, been found that the stabilizing methods known in the Korean Patents have several problems as followings; The process for preparing core material and forming enteric-coating is very complicated. The stabilized omeprazole is discolored and degraded during stay in stomach after oral administration, because gastric juice passes through the enteric-coating to partially dissolve the watersoluble internal layer and then infiltrated into the core to dissolve the alkaline substance partially destroying the enteric-coating. The stability of omeprazole by this process is not secured concretely. For formulating omeprazole, it is necessary to give good attention to omeprazole itself. For example, it must be kept at below $-20°$ C. of low temperature and immediately used for formulating after removing moisture, or immediately after synthesis, to maintain the starting stability.

After all, tier stabilizing the acid-unstable compound a primary factor is not only to secure the stability of preparation but also to stabilize the compound itself. Thus the attempt to stabilize acid-unstable compound must take into account the stability of the compound during the stablization process, its stability against gastric juice and the need to quickly and completely dissolve are made the available main drug for absorption in the intestine.

As discussed above most of the previously described methods are either very partially successful in stabilization or the stable inclusion compound is not produced at all conjugation attempt to add alkaline salt to omeprazole have also been unsatisfactory.

SUMMARY OF THE INVENTION

The object of the present invention is to obtain oral drugs of acid-unstable compound, having excellent storage stability, dissolution and absorption properties after oral administration and a simplified manufacturing process principally involving formation of inclusion complex by reacting the acid-unstable compound with cyclodextrin to give stabilized compound.

The present invention is a method for preparing enteric-coated oral drugs by using cyclodextrin to stabilize acid-unstable compound, characterized in which acid-unstable compound is reacted with cyclodextrin of $1 \sim 10$ mole based on 1 mole of acid-unstable compound in an alkaline solution to obtain inclusion complex without existence of alkaline substance.

DETAILED DESCRIPTION OF THE INVENTION

The present invention is accomplished by using a new solution system, instead of organic solvent such as ethanol used in prior art, in which acid-unstable compound is reacted with cyclodextrin for stabilizing. The alkaline solution used in the present invention performs a different function from alkaline solvent in prior art. As a result the inclusion complex obtained by the present invention dose not include the alkaline components.

According to the present invention when acid-unstable compound is reacted with cyclodextrin in alkaline solution, the reaction is carried out under homogeneous solution system for $1 \sim 30$ mins at $40° \sim 70°$ C., and after cooling to room temperature the reacted solution is allowed to stand at $4°$ C. to deposit inclusion complex. The reactant is filtered to remove residual alkaline component and to obtain pured stable inclusion complex as the desired product.

In the above reaction, if the temperature is below $40°$ C., since the solubility of cyclodextrin is decreased and an excessive of alkaline solution is needed, the reaction scale becomes unnecessarily large and the yield is decreased, and if the reaction temperature is more than $70°$ C., acid-unstable compound may be discolored or degraded.

Furthermore, under the condition if the reaction time is below 1 min, acid-unstable compound and cyclodextrin not are entirely dissolved in the alkaline solution, and if the reaction time over 30 mins, acid-unstable compound is also discolored and degraded.

In the present invention, benzimidazole derivative having the following structural formula(I) and pharmaceutically acceptable salt thereof, especially omeprazole and its sodium salt, is preferably used as acid-unstable compound.

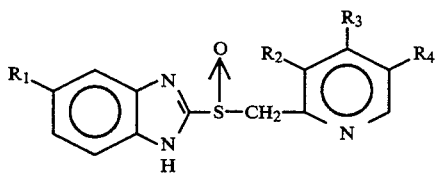

Wherein, $R_1$ is selected from the group consisting of hydrogen atom, methoxy, trifluoromethyl and tetrafluoroethoxy group;

$R_2$ is selected from the group consisting of hydrogen atom, methylamine and dimethylamine group;

$R_3$ is selected from the group consisting of hydrogen atom, methoxy, aryloxy and propaziloxy group; and $R_4$ is hydrogen atom or methyl group.

A pharmaceutical preparation containing said acid-unstable compounds in pharmaceutically effective amount may be prepared by the present invention in form of dosage units for oral administration such as tablets, granules, capsules, spherical pellets, microgranules, or microcapsules.

According to the present invention, acid-unstable compound is reacted with cyclodextrin structurally having hydrophobic cavity of a defined size, and at this time an inclusion complex is obtained because of the property of cyclodextrin to protect hydrophobic compounds from outside by entrapping them into the cavity. Cyclodextrin may be prepared by resolving starch with cyclodextrin glycosyltransferase and are classified according to the properties and size shown as following Table A. In accordance with the present invention, a cyclodextrin(CD) selected from the group consisting of α-, β- and δ-cyclodextrin, and cyclodextrin derivatives such as methyl-β-cyclodextrin, hydroxyethyl β-cyclodextrin, hydroxypropyl α-cyclodextrin, hydroxypropyl β-cyclodextrin, hydroxypropyl δ-cyclodextrin, etc. may be used.

TABLE A

| Comparison of Properties for Natural Cyclodextrins | | | |
|---|---|---|---|
| Properties | α-CD | β-CD | γ-CD |
| A Number of Glucose Units | 6 | 7 | 8 |
| Molecular Weight | 973 | 1135 | 1297 |
| Solubility in 25° C. Water (g/100 ml) | 14.5 | 1.85 | 23.2 |
| Cavity Diameter (Å) | 4.7–5.3 | 6.0–6.5 | 7.5–8.3 |
| Ring-opening Half-life (h)* | 6.2 | 5.4 | 3.0 |

*(Note) Ring-opening half-life was measured under the condition of 60° C., 1N HCl.

In the present invention, to obtain stable inclusion complex powder, the used alkaline solution is a aqueous solution of one selected from the group consisting of hydroxides of alkaline metal, alkaline salts of organic or inorganic acid, amines, buffer solutions, and a mixture thereof.

The alkaline compounds in the present invention as alkaline aqueous solution may be typically illustrated as followings: Hydroxide of alkaline metal may be selected from the group consisting of sodium hydroxide, potassium hydroxide, calcium hydroxide and barium hydroxide. Alkaline salt of organic acid may be sodium acetate or sodium citrate. Alkaline salt of inorganic acid may be selected from the group consisting of sodium borate, sodium carbonate, sodium phosphate, potassium borate, potassium carbonate and potassium phosphate. Amines may be selected from the group consisting of diethylamine, triethylamine, butylamine, ethylenediamine, triethanolamine, propylamine, dipropylamine, diethanolamine, monoethanolamine, isobutylamine, diisopropylamine, tert-butylamine, dibutylamine, diisobutylamine, tributylamine, pentylamine and dipentylamine. Buffer solution may be selected from the group consisting of carbonate buffer solution, phosphate buffer solution, borate buffer solution and tris buffer solution.

When the aqueous solution of hydroxide of alkaline metal, alkaline salt of organic or inorganic acid, or buffer solution are used as alkaline solution, the lower pH of alkaline solution affects the acid-unstable compound which may be discolored or to degraded during stabilizing reaction. Also, the higher pH of the reaction solution requires longer water-washing time to obtain neutral inclusion complex of acid-unstable compound included in cyclodextrin and the yield is decreased due to partially washing out the inclusion complex during the water-washing. Therefore, alkaline solution may be preferably used between pH 8.0 and 12.0.

In the case of independently using amine in alkaline solution, an amine water solution of 0.01~0.5M may be preferably used to form inclusion complex under stable condition and to reduce after-treatment time.

On the other hand, the above cyclodextrin in the present invention is preferably used in a ratio of 1~10 mole based on 1 mole of acid-unstable compound. If the used amount of cyclodextrin is below 1.0 mole, unincluded acid-unstable compound is remain in excess of quantity, and if over 10 mole, the amount of acid-unstable compound in the obtained inclusion complex is decreased by existence of unreacted cyclodextrins.

In accordance with the present invention the clear solution obtained by the above reaction is cooled to low temperature(4° C.) and maintained for 3~15 hours at that temperature to afford the desired inclusion complex formation as microcrystalline powder. The cooling of reaction mixture to give inclusion complex must be very carefully observed to see how the crystalline deposit is formed. If the treating time is below 3 hours, inclusion complex is not sufficiently deposited, and if over 15 hours, the productivity of desired product is decreased and the inclusion complex may be discolored in the reacted solution.

The obtained inclusion complex is washed with some cooled-water several times to completely remove the remaining alkaline component on the inclusion complex, and then the refined complex of neutrality is obtained. Otherwise, the reacted solution may be purified by spray drying, freeze drying, vacuum evaporating or recrystalline method to obtain a refined inclusion complex power as stable compound, and at this time the refining process may be carried out as per prior art according to properties of solusion system, namely kind of solution.

The above inclusion complex obtained by the present invention is to obviously improve storage stability of compound itself, and simultaneously to entirely maintain the stability during formulating process and in gastric juice with excellent dissolution and absorption properties. In the stabilized inclusion complex, there is no alkaline component, because the alkaline solution according to the present invention was only used as reacting solution in the stabilizing process. This process is different in the used art and objective because the core material obtained is free from alkali component common with prior art.

In the formulation of pharmaceutical preparation containing the inclusion complex of the present invention in the form of dosage units for oral administration, the above inclusion complex may be mixed with excipients such as microcrystalline cellulose, starch, manitol, etc., disintegrants such as sodium starch glycolate, etc. and lubricants such as magnesium stearate. The mixture is then pressed into tablets including active component, for example omeprazole of 20 mg per tablet. The prepared tablets may be coated with a watersoluble substance selected from the group consisting of hydroxypropyl methylcellulose, hydroxypropyl cellulose, polyvinylidone and polyvinylalcohol, and thereafter coated with an enteric-coating agent selected from the group consisting of hydroxypropylmethyl cellulose phthalate, celluloseacetate phthalate and metacrylic acid-methyl metacrylate copolymer, which is mixed with plasticizer in organic solvent.

The enteric-coated oral drugs formulated according to the present invention may be, as stabilized preparation including acid-unstable compound as active component, therapeutically administrated for the treatment of gastrointestinal disorders. The process described herein is successful in improving stability of acid-unstable compounds against acid, improves dissolution properties and improve preservability. Especially in case of omeprazole, this process entirely resolves the problems related to stability.

The followings illustrate a preferred embodiment of the present invention without being limited thereto.

PREPARING EXAMPLE 1

Buffer Solution(Phosphate)

To prepare an alkaline solution for stabilizing acid-unstable compound, 0.1M NaOH was added in 500 ml of 0.1M $KH_2PO_4$ as following Table 1.

Those solutions were diluted with water to obtain phosphate buffer solutions of each 1000 ml. Each pH of the resulted buffer solutions was measured to be selectively used for an alkaline solution.

TABLE 1

| Preparing Ex. 1 | 0.1M NaOH (ml) | pH |
|---|---|---|
| 1-1 | 224 | 6.8 |
| 1-2 | 291 | 7.0 |
| 1-3 | 347 | 7.2 |
| 1-4 | 391 | 7.4 |
| 1-5 | 428 | 7.6 |
| 1-6 | 453 | 7.8 |
| 1-7 | 467 | 8.0 |

PREPARING EXAMPLE 2

Buffer Solution(Borate)

0.1M NaOH was added in 500 ml of 0.1M $H_3BO_3$—KCl to obtain borate buffer solutions according to the above Preparing Example 1 as following Table 2. Each pH of the resulted buffer solutions was measured to be selectively used for an alkaline solution.

TABLE 2

| Preparing Ex. 2 | 0.1M NaOH (ml) | pH |
|---|---|---|
| 2-1 | 39 | 8.0 |
| 2-2 | 60 | 8.2 |
| 2-3 | 86 | 8.4 |
| 2-4 | 118 | 8.6 |
| 2-5 | 158 | 8.8 |
| 2-6 | 208 | 9.0 |
| 2-7 | 264 | 9.2 |
| 2-8 | 321 | 9.4 |
| 2-9 | 369 | 9.6 |
| 2-10 | 406 | 9.8 |
| 2-11 | 437 | 10.0 |
| 2-12 | 462 | 10.2 |

PREPARING EXAMPLE 3

Tris Buffer Solution 0.1M HCl was added in 500 ml of 0.1M tris(hydroxymethyl) amino methane to obtain amine salt buffer solutions according to the above Preparing Example 1 as following Table 3. Each part of the resulted buffer solutions was measured to be selectively used for an alkaline solution.

TABLE 3

| Preparing Ex. 3 | 0.1M HCl (ml) | pH |
|---|---|---|
| 3-1 | 466 | 7.0 |
| 3-2 | 447 | 7.2 |
| 3-3 | 420 | 7.4 |
| 3-4 | 385 | 7.6 |
| 3-5 | 345 | 7.8 |
| 3-6 | 292 | 8.0 |
| 3-7 | 229 | 8.2 |
| 3-8 | 172 | 8.4 |
| 3-9 | 124 | 8.6 |
| 3-10 | 85 | 8.8 |
| 3-11 | 57 | 9.0 |

PREPARING EXAMPLE 4

Buffer Solution (Borate)

0.1M HCl was added in 500 ml of 0.025M $Na_2B_4O_7$ to obtain borate buffer solutions according to the above Preparing Example 1 as following Table 4. Each pH of the resulted buffer solutions was measured to be selectively used for an alkaline solution.

TABLE 4

| Preparing Ex. 4 | 0.1M HCl (ml) | pH |
|---|---|---|
| 4-1 | 205 | 8.0 |
| 4-2 | 188 | 8.2 |
| 4-3 | 166 | 8.4 |
| 4-4 | 135 | 8.6 |
| 4-5 | 94 | 8.8 |
| 4-6 | 46 | 9.0 |

PREPARING EXAMPLE 5

Buffer Solution (Borate)

0.1M NaOH was added in 500 ml of 0.025M $Na_2B_4O_7$ to obtain borate buffer solutions according to the above Preparing Example 1 as following Table 5. Each pH of the resulted buffer solutions was measured to be selectively used for an alkaline solution.

TABLE 5

| Preparing Ex. 5 | 0.1M NaOH (ml) | pH |
|---|---|---|
| 5-1 | 9 | 9.2 |
| 5-2 | 62 | 9.4 |

TABLE 5-continued

| Preparing Ex. 5 | 0.1M NaOH (ml) | pH |
|---|---|---|
| 5-3 | 111 | 9.6 |
| 5-4 | 150 | 9.8 |
| 5-5 | 183 | 10.0 |
| 5-6 | 205 | 10.2 |
| 5-7 | 221 | 10.4 |
| 5-8 | 233 | 10.6 |
| 5-9 | 242.5 | 10.8 |

PREPARING EXAMPLE 6

Buffer Solution (Carbonate)

0.1M NaOH was added in 500 ml of 0.05M $NaHCO_3$ to obtain carbonate buffer solutions according to the above Preparing Example 1 as following Table 6. Each pH of the resulted buffer solutions was measured to be selectively used for an alkaline solution.

TABLE 6

| Preparing Ex. 6 | 0.1M NaOH (ml) | pH |
|---|---|---|
| 6-1 | 50 | 9.6 |
| 6-2 | 76 | 9.8 |
| 6-3 | 107 | 10.0 |
| 6-4 | 138 | 10.2 |
| 6-5 | 165 | 10.4 |
| 6-6 | 191 | 10.6 |
| 6-7 | 212 | 10.8 |
| 6-8 | 227 | 11.0 |

PREPARING EXAMPLE 7

Buffer Solution (Phosphate)

0.1M NaOH was added in 500 ml of 0.05M $Na_2HPO_4$ to obtain phosphate buffer solutions according to the above Preparing Example 1 as following Table 7. Each pH of the resulted buffer solutions was measured to be selectively used for an alkaline solution.

TABLE 7

| Preparing Ex. 7 | 0.1M NaOH (ml) | pH |
|---|---|---|
| 7-1 | 41 | 11.0 |
| 7-2 | 63 | 11.2 |
| 7-3 | 91 | 11.4 |
| 7-4 | 135 | 11.6 |
| 7-5 | 194 | 11.8 |
| 7-6 | 269 | 12.0 |

PREPARING EXAMPLE 8

Buffer Solution (Chlorate)

0.2M NaOH was added in 250 ml of 0.2M KCl to obtain chlorate buffer solutions according to the above Preparing Example 1 as following Table 8. Each pH of the resulted buffer solutions was measured to be selectively used for an alkaline solution.

TABLE 8

| Preparing Ex. 8 | 0.2M NaOH (ml) | pH |
|---|---|---|
| 8-1 | 60 | 12.0 |
| 8-2 | 102 | 12.2 |
| 8-3 | 162 | 12.4 |
| 8-4 | 256 | 12.6 |
| 8-5 | 412 | 12.8 |
| 8-6 | 660 | 13.0 |

The obtained buffer solutions may be preferably used in range of pH 8.0~12.0 for alkaline solution, and hydroxides of alkaline metal or alkaline salt of organic or inorganic salt may be also used by adjusting to range of pH 8.0~12.0.

But, it is necessary for amines to define the preferable range of alkaline solution by molarity. According to the present invention, water-soluble or water-miscible amines shown on following Table 9, preferably 0.01~0.5M amines, may be preferably used, but methylamine, dimethyl amine, trimethylamine, ethylamine, isopropylamine, etc. were excluded from studies because of having low boiling point.

TABLE 9

| Amines | b.p. (°C.) | pKa |
|---|---|---|
| Diethylamine | 55.5 | 10.98 |
| Triethylamine | 89–90 | 11.01 |
| Butylamine | 77 | 10.77 |
| Ethylenediamine | 116–117 | 10.71 |
| Triethanolamine | 335.4 | 9.50 |
| Propylamine | 48–49 | 10.57 |
| Dipropylamine | 110 | 11.0 |
| Diethanolamine | 268.8 | 8.88 |
| Monoethanolamine | 170.8 | 9.50 |
| Isobutylamine | 68–69 | 10.42 |
| Diisopropylamine | 83.5 | 11.05 |
| Tert-butylamine | 43.6 | 10.87 |
| Dibutylamine | 159.6 | 11.31 |
| Diisobutylamine | 136–140 | 10.5 |
| Tributylamine | 91–92 (9 mmHg) | 10.87 |
| Pentylamine | 104 | 10.63 |
| Dipentylamine | 91–93 (14 mmHg) | 11.18 |

EXAMPLE 1

β-Cyclodextrin of 24 g was dissolved in each 900 ml of buffer solutions according to following Table 10 at 40° C., and 3.4 g omeprazole was added in the solution under stirring to react for 15 mins.

The reactant was concentrated to 100 ml in vacuum evaporator, and after cooling to room temperature, it was left for 6 hrs in a refrigerator to deposit inclusion complex. The filtered inclusion complex was washed with water several times and dried under reduced pressure to obtain omeprazole-cyclodextrin inclusion complex.

The result of reaction and an amount of the obtained inclusion complex were shown as following Table 10.

TABLE 10

| Example 1 | Buffer solution | pH | Inclusion Complex Color | Inclusion Complex Amount |
|---|---|---|---|---|
| 1-A | Preparing Ex. 1-2 | 7.0 | ± | 24.2 |
| 1-B | Preparing Ex. 2-1 | 8.0 | ± | 24.9 |
| 1-C | Preparing Ex. 2-6 | 9.0 | — | 25.9 |
| 1-D | Preparing Ex. 2-11 | 10.0 | — | 26.2 |
| 1-E | Preparing Ex. 6-8 | 11.0 | — | 26.0 |
| 1-F | Preparing Ex. 7-6 | 12.0 | — | 25.3 |
| 1-G | Preparing Ex. 8-6 | 13.0 | — | 24.5 |

(Note)
—: Non discoloration
±: Light-violet color

As the result shown in Table 10, it was found that when pH is low the inclusion complex is discolored to light-violet color, and when pH is high the obtained amount of inclusion complex is decreased due to washing with excess water. Therefore a buffer solution was preferably selected between pH 8.0 and pH 12.0 for an alkaline solution.

EXAMPLE 2

β-Cyclodextrin of 24 g was dissolved in each 900 ml of buffer solutions (pH 9.0, pH 10.0, pH 11.0) according to following Table 11 at 40° C., and 3.4 g omeprazole was added in the solution under stirring to react for 15 mins.

The reactant was concentrated to 100 ml in vacuum evaporator, and after cooling to room temperature, it was left for 6 hrs in a refrigerator to deposit inclusion complex. The filtered inclusion complex was washed with water several times and dried under reduced pressure to obtain omeprazole-cyclodextrin inclusion complex.

The results of reaction were shown as following Table 11.

TABLE 11

| Example 1 | Buffer solution | pH | Color of Inclusion Complex | Rate of Inclusion (%) |
|---|---|---|---|---|
| 2-A | Preparing Ex. 2-6 | 9.0 | — | 89.0 |
| 2-B | Preparing Ex. 3-11 | 9.0 | — | 91.2 |
| 2-C | Preparing Ex. 4-6 | 9.0 | — | 90.1 |
| 2-D | Preparing Ex. 2-11 | 10.0 | — | 98.6 |
| 2-E | Preparing Ex. 5-5 | 10.0 | — | 99.1 |
| 2-F | Preparing Ex. 6-3 | 10.0 | — | 98.9 |
| 2-G | Preparing Ex. 6-8 | 11.0 | — | 99.2 |
| 2-H | Preparing Ex. 7-1 | 11.0 | — | 98.8 |

(Note)
—: Non discoloration

As the result shown in Table 11, it is was found that when pH of buffer solution is the same the effectiveness of inclusion is not influenced by kind of buffer solution, and when it is more than pH 10 the rate of inclusion was higher than 98.6%.

EXAMPLE 3

β-Cyclodextrins according to following Table 12 were respectively dissolved in 900 ml of buffer solutions (pH 10.0) prepared by the above Preparing Example 2-11 to add omeprazole, and then the reaction temperature was changed to 40° C., 50° C., 60° C., and 70° C. as the reaction being carried out for 15 mins.

The reactant was concentrated to 100 ml in vacuum evaporator, and after cooling to room temperature, it was left for 6 hrs in a refrigerator to deposit inclusion complex. The filtered inclusion complex was washed with water on several times and dried under reduced pressure to obtain omeprazole-cyclodextrin inclusion complex. The results of reaction were shown as following Table 12.

TABLE 12

| Example 3 | Reaction Temp. (°C.) | Amount of β-CD (g) | Amount of Omeprazole (g) | Color of Inclusion complex | Rate of Inclusion (%) |
|---|---|---|---|---|---|
| 3-A | 40 | 24.0 | 3.4 | — | 98.6 |
| 3-B | 50 | 54.0 | 8.2 | — | 98.8 |
| 3-C | 60 | 85.0 | 12.9 | — | 99.0 |
| 3-D | 70 | 135.0 | 20.5 | — | 98.0 |

(Note)
—: Non discoloration
β-CD: β-cyclodextrin

EXAMPLE 4

β-Cyclodextrines according to following Table 13 were respectively dissolved in 900 ml of buffer solution (pH 10.0) prepared by the above Preparing Example 2-11 at 50° C., and omeprazole was added in the solution under stirring to react for 15 mins.

The reactant was concentrated to 100 ml in vacuum evaporator, and after cooling to room temperature, it was left for 6 hrs in a refrigerator to deposit inclusion complex. The filtered inclusion complex was washed with water on several times and dried under reduced pressure to obtain omeprazole-cyclodextrin inclusion complex. The results of reaction were shown as following Table 13.

TABLE 13

| Example 4 | Kind of CD | Amount of CD (g) | Amount of Omeprazole (g) | Rate of Inclusion (%) |
|---|---|---|---|---|
| 4-A | α-CD | 4.2 | 5.9 | 97.2 |
| 4-B | HP-α-CD | 1.8 | 0.25 | 98.0 |
| 4-C | β-CD | 54.0 | 8.2 | 98.8 |
| 4-D | HP-β-CD | 1.5 | 0.17 | 99.2 |
| 4-E | HE-β-CD | 1.95 | 0.23 | 99.0 |
| 4-F | M-β-CD | 2.4 | 0.3 | 98.5 |
| 4-G | γ-CD | 7.0 | 0.74 | 99.1 |
| 4-H | HP-γ-CD | 2.4 | 0.25 | 99.0 |

(Note)
CD: Cyclodextrin
HP: Hydroxypropyl
HE: Hydroxyethyl
M: Methyl

EXAMPLE 5

β-cyclodextrin of 54 g was dissolved in each 900 ml of 0.1M amine aqueous solutions according to following Table 9 at 50° C., and 8.2 g omeprazole was added in the solution under stirring to react for 15 mins.

The reactant was cooled to room temperature and/or concentrated to 100 ml in vacuum evaporator, and it was left for 6 hrs in a refrigerator to deposit inclusion complex.

The filtered inclusion complex was washed with water several times and dried under reduced pressure to obtain omeprazole-cyclodextrin inclusion complex. The results of reaction were shown as following Table 14.

TABLE 14

| Example 5 | Kind of Amine | Deposition Method | Rate of Inclusion (%) |
|---|---|---|---|
| 5-A | Diethylamine | Cool | 89.2 |
| 5-B | Triethylamine | Cool/Conc. | 95.7 |
| 5-C | Propylamine | Cool | 90.3 |
| 5-D | Dipropylamine | Conc. | 98.0 |
| 5-E | Isobutylamine | Cool | 89.7 |
| 5-F | Diisopropylamine | Cool/Conc. | 92.3 |
| 5-G | Butylamine | Cool | 96.7 |
| 5-H | Ethylenediamine | Conc. | 97.1 |
| 5-I | Mono-ethanolamine | Conc. | 98.9 |
| 5-J | Diethanolamine | Conc. | 99.1 |
| 5-K | Triethanolamine | Conc. | 99.1 |
| 5-L | Tert-butylamine | Cool | 89.0 |
| 5-M | Dibutylamine | Conc. | 97.3 |
| 5-N | Diisobutylamine | Conc. | 96.8 |
| 5-O | Tributylamine | Conc. | 98.3 |
| 5-P | Pentylamine | Conc. | 98.7 |
| 5-Q | Dipentylamine | Conc. | 99.3 |

(Note)
Cool: Cooling to room temperature
Conc.: Concentrating in vacuum evaporator

EXAMPLE 6

According to following Table 15, β-cyclodextrin was dissolved in 900 ml water, and on the other hand omeprazole was dissolved in 40% (v/v) triethylamine aqueous solution to obtain 27% solution. The resulted omeprazole solution was dropwise added in cyclodextrin aqueous solution.

The reactant was cooled to room temperature, and left for 6 hrs in a refrigerator to deposit inclusion complex.

The filtered inclusion complex was washed with water several times and dried under reduced pressure to obtain omeprazole-cyclodextrin inclusion complex. The results of reaction were shown as following Table 15.

TABLE 15

| Example 6 | Reaction Temp. (°C.) | Amount of $\beta$-CD (g) | Amount of Omeprazole (g) | Rate of Inclusion (%) |
|---|---|---|---|---|
| 6-A | 40 | 24.0 | 3.4 | 99.5 |
| 6-B | 50 | 54.0 | 8.2 | 99.1 |
| 6-C | 60 | 85.0 | 12.9 | 98.1 |
| 6-D | 70 | 135.0 | 20.5 | 98.5 |

EXAMPLE 7

24 g $\beta$-cyclodextrin was dissolved in 900 ml of pH 12 aqueous solutions of hydroxide of alkaline metals according to following Table 16, and 3.4 g omeprazole was added in this solution under stirring to react for 15 mins.

The reactant was concentrated to 100 ml in vacuum evaporator, and after cooling to room temperature, it was left for 6 hrs in a refrigerator to deposit inclusion complex.

The filtered inclusion complex was washed with water several times and dried under reduced pressure to obtain omeprazole-cyclodextrin inclusion complex. The results of reaction were shown as following Table 16.

TABLE 16

| Example 7 | Kind of Hydroxide | Reaction Temp. (°C.) | Amount of $\beta$-CD (g) | Amount of Omeprazole (g) | Rate of Inclusion (%) |
|---|---|---|---|---|---|
| 7-A | NaOH | 40 | 24.0 | 3.4 | 99.3 |
| 7-B | KOH | 40 | 24.0 | 3.4 | 99.1 |
| 7-C | Ca(OH)$_2$ | 40 | 24.0 | 3.4 | 98.8 |
| 7-D | Ba(OH)$_2$ | 40 | 24.0 | 3.4 | 98.7 |

EXAMPLE 8

This experiment was conducted in same manner as previous Example 7 except that the other alkaline salt solutions according to following Table 17 were used to obtain omeprazole-dextrin inclusion complex.

The filtered inclusion complex was washed with water several times and dried under reduced pressure to obtain omeprazole-cyclodextrin inclusion complex. The results of reaction were shown as following Table 17.

Methods for Measuring Rate of Inclusion $$\frac{\text{Amount of omeprazole in the obtained inclusion complex (g)}}{\text{Amount of used omeprazole (g)}} \times 100 = \text{Rate of inclusion (\%)}$$

The amount of omeprazole in the obtained inclusion complex was measured by HPLC under following conditions.

Solvent: pH 9.8 Carbonate buffer solution: ethanol = 80:20

Column: $\mu$-Bondapak $C_{18}$ 3.9 mm (the inside diameter) × 300 mm (length)

Mobile Phase: pH 7.6 Phosphate buffer solution: Acetonitrile = 66:34

Detection Wave-length: 302 nm

Injection Volume :20 $\mu$l

Flow Rate: 1.0 ml/min

COMPARATIVE EXAMPLE 1

5.67 g $\beta$-cyclodextrin and 1.73 g omeprazole were added in 96% ethanol of 20 ml and stirred at 30° ~32° C. for 15 hrs.

After leaving at 10° C. for 3 hrs, the reacted solution was filtered, and washed with ethanol of 10° C., dried under reduced pressure to obtain the desired product of reddish brown color. At this time the reactant solution was of purple color.

COMPARATIVE EXAMPLE 2

2.0 g Omeprazole was well mixed with 2.0 g Na$_2$HPO$_4$, and the mixed compound was dried under reduced pressure to obtain the stabilized core of omeprazole preparation as a comparative sample.

COMPARATIVE EXAMPLE 3

This test was conducted in process of the above Comparative Example 2 except to use 2.0 g omeprazole and 2.0 g Mg(OH)$_2$. The obtained core was used as a comparative sample.

EXPERIMENTAL EXAMPLE 1

Storage Stability of Inclusion Complex

To verify stabilized result for the above Example 1 to 8 and Comparative Example 1 to 3, the change of appearance was surveyed with the passing of time under 40° C., 75% RH of accelerated condition. The results were shown on following Table 18.

Under the above condition, storage stability during 6 months means to secure stability for 3 years at normal condition. As the result of Table 18, it was confirmed that the cases of Example 1~8 according to the present invention is obviously showing higher stability than the cases of Comparative Example 1~3.

TABLE 17

| Example 8 | Kind of alkaline salts | pH | Reaction Temp. (°C.) | Amount of $\beta$-CD (g) | Amount of Omeprazole (g) | Rate of Inclusion (%) |
|---|---|---|---|---|---|---|
| 8-A | Na$_2$B$_4$O$_7$ | 10.0 | 40 | 24.0 | 3.4 | 99.2 |
| 8-B | K$_2$B$_4$O$_7$ | 10.0 | 40 | 24.0 | 3.4 | 99.3 |
| 8-C | Na$_2$CO$_3$ | 10.0 | 40 | 24.0 | 3.4 | 99.8 |
| 8-D | K$_2$CO$_3$ | 10.0 | 40 | 24.0 | 3.4 | 99.5 |
| 8-E | Na$_2$HPO$_4$ | 10.0 | 40 | 24.0 | 3.4 | 99.1 |
| 8-F | K$_2$HPO$_4$ | 10.0 | 40 | 24.0 | 3.4 | 99.3 |
| 8-G | CH$_3$COONa | 8.5 | 40 | 24.0 | 3.4 | 98.7 |
| 8-H | Sodium citrate | 9.0 | 40 | 24.0 | 3.4 | 98.5 |

TABLE 18

| Sample | The Change of Appearance | | | | |
|---|---|---|---|---|---|
| | Start | After 1 month | After 2 months | After 4 months | After 6 months |
| Example 1-D | — | — | — | — | — |
| Example 2-B | — | — | — | — | — |
| Example 2-E | — | — | — | — | — |
| Example 2-G | — | — | — | — | — |
| Example 3-A | — | — | — | — | — |
| Example 3-D | — | — | — | — | — |
| Example 4-A | — | — | — | — | — |
| Example 4-B | — | — | — | — | — |
| Example 4-D | — | — | — | — | — |
| Example 4-E | — | — | — | — | — |
| Example 4-F | — | — | — | — | — |
| Example 4-G | — | — | — | — | — |
| Example 4-H | — | — | — | — | — |
| Example 5-B | — | — | — | — | — |
| Example 5-I | — | — | — | — | — |
| Example 6-A | — | — | — | — | — |
| Example 6-D | — | — | — | — | — |
| Example 7-A | — | — | — | — | — |
| Example 8-C | — | — | — | — | — |
| Comp. Ex. 1 | + | ++ | ++ | ++ | ++ |
| Comp. Ex. 2 | — | ± | + | ++ | ++ |
| Comp. Ex. 3 | — | — | ± | + | + |

(Note)
—: Non discoloration
±: Some discoloration
+: Discoloration
++: Deep discoloration

Formulation of Inclusion Complex

To formulate enteric-coated oral drugs, the omeprazole-cyclodextrin inclusion complexes obtained by Example 1~8 were used as followings.

Preparing of Uncoated Tablets

According to following Table 19, omeprazole of 20 mg was homogeneously mixed with excipients, disintegrants and lubricants, and the mixture was tableted to 230 mg per unit by Rotary Tableting Machine.

TABLE 19

| Mixed Components | (Unit: mg) Example No. | | | | | | | |
|---|---|---|---|---|---|---|---|---|
| | 1-D | 2-E | 3-B | 4-A | 5-I | 6-B | 7-A | 8-C |
| Inclusion complex | 165 | 165 | 165 | 165 | 165 | 165 | 165 | 165 |
| Microcrystalline cellulose | 42 | 40 | 30 | 30 | 23 | 20 | 20 | 20 |
| Dibasic calcium phosphate Anhydrous | 20 | 15 | 10 | 5 | — | 5 | — | — |
| Corn starch | — | 7 | 22 | 27 | 24.7 | 20 | 12.7 | — |
| Mannitol | — | — | — | — | — | 7.7 | 15 | 27.7 |
| Sodium starch glycolate | — | — | — | — | 15 | 10 | 15 | 15 |
| Magnesium stearate | 3.0 | 3.0 | 3.0 | 3.0 | 2.3 | 2.3 | 2.3 | 2.3 |

In the above, when microcrystalline cellulose and dibasic calcium phosphate anhydrous of an excess of quantity were used, hardness of tablets is excellent but disintegration rate was decreased. Therefore, microcrystalline cellulose of small amount was preferably used, and at that time the used amount of corn starch and/or Mannitol were increased and minimum amount of dibasic calcium phosphate anhydrous was used.

Coating of Watersoluble Substance

According to following Table 20, a watersoluble substance was coated on uncoated tablets.

TABLE 20

| Components of Watersoluble Substance | (Unit: mg) | | | | | | | | |
|---|---|---|---|---|---|---|---|---|---|
| | (T₁) | (T₂) | (T₃) | (T₄) | (T₅) | (T₆) | (T₇) | (T₈) | (T₉) |
| Hydroxy propylmethyl cellulose | 10 | 9 | 9 | 9 | 9 | 9 | — | — | — |
| Hydroxypropyl cellulose | — | — | — | — | — | — | 9 | — | — |
| Polyvinylpyrrolidone | — | — | — | — | — | — | — | 9 | — |
| Polyvinylalcohol | — | — | — | — | — | — | — | — | 9 |
| Propyleneglycol | — | 1 | — | — | 1 | — | — | — | — |
| Polyethyleneglycol 600 | — | — | 1 | — | — | 1 | 1 | 1 | 1 |
| Water | 190 | 190 | 190 | 38 | 38 | 38 | 38 | 38 | 38 |
| Ethanol | — | — | — | 152 | 152 | 152 | 152 | 152 | 152 |

In the above test, when water was only used as solvent or excessive water was used, dry time in coating pan was prolonged.

Since tablets were observed to stick with each other and rendering the coating surface ununiform, ethanol, preferably 80% ethanol water solution, was used in this process as main solvent.

Coating of Enteric Substance

According to following Table 21, an enteric substance was coated on tablets coated with watersoluble substance to obtain the desired enteric-coated oral drug.

TABLE 21

| Components of Enteric Substance | a | b | c | d | e |
|---|---|---|---|---|---|
| Hydroxypropylmethyl cellulose phthalate | 18.6 | — | — | 18.6 | — |
| Cellulose acetate phthalate | — | 18.6 | — | — | 18.6 |
| Eudragit L100 | — | — | 18.0 | — | — |
| Cetylalcohol | 1.4 | 1.4 | — | — | — |
| Myvacet 9-40T | — | — | — | 1.4 | 1.4 |
| Dibutylphthalate | — | — | 2.0 | — | — |
| Acetone | 152 | 190 | 152 | 152 | 190 |
| Ethylalcohol | 228 | 190 | — | 228 | 190 |
| Isopropylalcohol | — | — | 228 | — | — |

EXPERIMENTAL EXAMPLE 2

Property Test for Oral Drugs

The obtained inclusion complexes of Examples were used to formulate enteric-coated oral drugs. To survey the properties for the oral drugs, the watersoluble substance according to the method of Table 20(T₅) was respectively coated on tablets prepared from Example 4-A, 5-I, 6-B, 7-A and 8-C, and there after the enteric substance according to the method of Table 21 "d" was coated on the above tablets.

The formulated oral drugs were compared with control product, Astra's LOSEC, to survey acid-resistance property, dissolution property, and storage stability as followings.

Test for Acid-resistance Property

The formulated oral drugs were put into artificial gastric fluid [USP, 1st solution] without enzyme and stirred at 37° C. by paddle at 100 rpm.

The test solution was left for 2 hrs to survey the change of appearance, and the omeprazole existing in preparation was measured by HPLC. The results were shown on following Table 22.

TABLE 22

| Testing Sample | Amount of the Existing Omeprazole (%) | The Change of Appearance |
|---|---|---|
| Example 4-A | 99.0 | Non discoloration |
| Example 5-I | 99.1 | " |
| Example 6-B | 99.5 | " |
| Example 7-A | 100.0 | " |
| Exmple 8-C | 99.2 | " |
| Control (Losec) | 96.7 | Brown spots in pellets |

The above test showed brown spots on 40~75% of pellets for the control(LOSEC), and it was also found that omeprazole content was decreased.

But, the oral drugs prepared according to examples were not affected in the appearance and omeprazole content was scarcely decreased, thus giving superior characteristics.

Test for Dissolution Property

To survey the rate of dissolution in the small intestines, the formulated oral drugs were added to simulated gastric fluid [USP, 37° C., 100 rpm].

After 2 hrs, the above drugs were moved to simulate intestinal fluid [USP, dissolution apparatus No. 2, Paddle Method], and then the amount of dissolved omeprazole was determined by the method of HPLC. The results were shown on Table 23.

TABLE 23

| | (Unit: %) Rate of Dissolution for Passing Time | | |
|---|---|---|---|
| Testing Sample | 10 min | 20 min | 30 min |
| Example 4-A | 85.9 | 97.6 | 99.2 |
| Example 5-I | 98.2 | 100.0 | 100.0 |
| Example 6-B | 90.3 | 98.0 | 99.5 |
| Example 7-A | 98.5 | 99.7 | 100.0 |
| Example 8-C | 98.0 | 99.2 | 99.8 |
| Control (Losec) | 91.5 | 92.0 | 93.5 |

As the result from the above experiment show, the dissolution rate for all samples was good only Example 4-A and 5-I produced using dibasic calcium phosphate anhydrous as excipient showed somewhat slow dissolution rate in first 10 minutes.

The rate of dissolution after 20 mins and 30 mins, testing samples of Examples were obviously higher than the control.

Test for Storage Stability

According to the process of Experiment Example 1, the drugs were kept in glass bottle for 6 months under 40° C., 75% RH of accelerated condition and 50° C., 75% RH of harsh condition.

The changes of appearance for the resulted samples were surveyed. The results were shown on Table 24.

TABLE 24

| | Test condition | |
|---|---|---|
| Testing Sample | 40° C., 75% RH | 50° C., 75% RH |
| Example 4-A | — | — |
| Example 5-I | — | — |
| Example 6-B | — | — |
| Example 7-A | — | — |
| Example 8-C | — | — |
| Control (Losec) | ± | ++ |

(Note)
—: Non discoloration
±: Some discoloration
+: Discoloration
++: Deep discoloration As the result of above, it was confirmed that the storage stabilities of Examples were obviously higher than the control.

As the result of Experimental Example 2, it was found that the enteric-coated oral drugs of the present invention formulated with omeprazol-cyclodextrin inclusion complex have excellent stability and dissolution property as compared with known preparations.

We claim:

1. A method for stabilizing an acid-unstable compound by forming an inclusion complex of omeprazole with cyclodextrin comprising:

dissolving cyclodextrin in an aqueous alkaline solution at 40°–70° C., and reacting said omeprazole with a cyclodextrin for 1 to 30 minutes in said alkaline solution, the ratio of said acid-unstable compound to said cyclodextrin in said reaction being from about 1:1 to about 1:10, on a number of moles basis.

2. In the method of claim 1, said alkaline solution consists essentially of an aqueous solution of an alkali selected from the group consisting of alkaline hydroxides, alkaline salts, amines, buffers, and combinations thereof.

3. In the method of claim 2, said alkaline hydroxide is selected from the group consisting of sodium hydroxide, potassium hydroxide, calcium hydroxide, barium hydroxide and combinations thereof.

4. In the method of claim 2, said alkaline salt is selected from the group consisting of sodium borate, sodium carbonate, sodium phosphate, potassium borate, potassium carbonate, potassium phosphate, sodium acetate, sodium citrate and combinations thereof.

5. In the method of claim 2, said amine is selected from the group consisting of diethylamine, triethylamine, butylamine, ethylenediamine, triethanolamine, propylamine, dipropylamine, diethanolamine, monoethanolamine, isobutylamine, diisopropylamine, tert-butylamine, dibutylamine, diisobutylamine, tributylamine, pentylamine, dipentylamine and combinations thereof.

6. In the method of claim 2, said buffer is selected from the group consisting of carbonate buffer, phosphate buffer, borate buffer, amine salt buffer, and combinations thereof.

7. A method for stabilizing a benzimidazole derivative having the following structural formula:

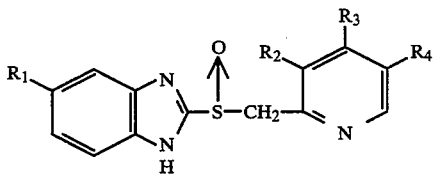

wherein:
R$_1$ is selected from the group consisting of hydrogen, methoxy, trifluoromethyl and tetrafluoroethoxy radicals;
R$_2$ is selected from the group consisting of hydrogen, methylamine and dimethylamine radicals;
R$_3$ is selected from the group consisting of hydrogen, methoxy, aryloxy and propaziloxy radicals; and
R$_4$ is selected from the group consisting of hydrogen and methyl radicals;
by forming an inclusion complex of said benzimidazole derivative with cyclodextrin comprising:
  A. Dissolving said cyclodextrin in an aqueous alkaline solution at a temperature between about 40° and 70° C.; and
  B. Reacting said cyclodextrin with said benzimidazole derivative for 1 to 30 minutes in said aqueous alkaline solution, the ratio of said benzimidazole derivative to said cyclodextrin being from about 1 to 10 moles of said cyclodextrin for each mole of said benzimidazole derivative.

8. In the method of claim 7, said alkaline solution consists essentially of an aqueous solution of an alkali selected from the group consisting of alkaline hydroxides, alkaline salts, amines, buffers and combinations thereof.

9. In the method of claim 8, said alkaline hydroxide is selected from the group consisting of sodium hydroxide, potassium hydroxide, calcium hydroxide, barium hydroxide and combinations thereof.

10. In the method of claim 8, said alkaline salt is selected from the group consisting of sodium borate, sodium carbonate, sodium phosphate, potassium borate, potassium carbonate, potassium phosphate, sodium acetate, sodium citrate and combinations thereof.

11. In the method of claim 8, said amine is selected from the group consisting of diethylamine, triethylamine, butylamine, ethylenediamine, triethanolamine, propylamine, dipropylamine, diethanolamine, monoethanolamine, isobutylamine, diisopropylamine, tert-butylamine, dibutylamine, diisobutylamine, tributylamine, pentylamine, dipentylamine and combinations thereof.

12. In the method of claim 8, said buffer is selected from the group consisting of carbonate buffer, phosphate buffer, borate buffer, amine salt buffer, and combinations thereof.

* * * * *

UNITED STATES PATENT AND TRADEMARK OFFICE
CERTIFICATE OF CORRECTION

PATENT NO. : 5,399,700

DATED : 21 March 1995

INVENTOR(S) : Song S. MIN et al.

It is certified that error appears in the above-identified patent and that said Letters Patent is hereby corrected as shown below:

| Column | Line | |
|---|---|---|
| 1 | 28 | Change "apprepri-" to --appropri- --. |
| 1 | 36 | Change "to form" to --a method of forming-- |
| 1 | 39 | Change "as" to --that--. |
| 1 | 62 | Change "as followings;" to --as follows:--. |
| 1 | 68 | Change "infiltrated" to --infiltrates--. |
| 2 | 9 | Change "tier" to --for--. |
| 2 | 16 | Change "are made the available main drug" to --so as to make the main drug available--. |
| 2 | 19 | Change "very" to --only--. |
| 2 | 21 | After "all" insert --, and--; change "attempt" to --attempts--. |

UNITED STATES PATENT AND TRADEMARK OFFICE
CERTIFICATE OF CORRECTION

PATENT NO. : 5,399,700

DATED : 21 March 1995

INVENTOR(S) : Song S. MIN et al.

It is certified that error appears in the above-identified patent and that said Letters Patent is hereby corrected as shown below:

| Column | Line | |
|---|---|---|
| 2 | 50 | Change "dose" to --does--. |
| 2 | 58 | Change "pured" to --purified--. |
| 3 | 2 | After "time" insert --is--. |
| 3 | 39 | Change "Cyclodextrin" to --Cyclodextrins--. |
| 3 | 41 | Change "as" to --in the--. |
| 3 | 44 | Change "ß-cyclodextrin" to --γ-cyclodextrin--. |
| 3 | 47 | Change "ß-cyclodextrin" to --γ-cyclodextrin--. |
| 3 | 60 | Change "a" to --an--. |
| 3 | 67 | Change "followings:" to --follows:--. |
| 4 | 20 | Before "degraded" delete "to". |

UNITED STATES PATENT AND TRADEMARK OFFICE
CERTIFICATE OF CORRECTION

PATENT NO. : 5,399,700

DATED : 21 March 1995

INVENTOR(S) : Song S. MIN et al.

It is certified that error appears in the above-identified patent and that said Letters Patent is hereby corrected as shown below:

| Column | Line | |
|---|---|---|
| 4 | 37 | Change "is remain in excess of" to --remains in excessive--. |
| 4 | 38 | Change "quanity" to --quantities--. |
| 4 | 55 | Change "on" to --from--. |
| 4 | 56 | Change "complex of neutrality" to --neutral complex--. |
| 4 | 59 | Change "recrystalline" to --recrystallization--. |
| 4 | 60 | Change "power" to --powder--. |
| 4 | 62 | Change "solusion" to --solution--. |
| 5 | 24 | Change "celluloseacetate" to --cellulose acetate--. |

UNITED STATES PATENT AND TRADEMARK OFFICE
CERTIFICATE OF CORRECTION

PATENT NO. : 5,399,700

DATED : 21 March 1995

INVENTOR(S) : Song S. MIN et al.

It is certified that error appears in the above-identified patent and that said Letters Patent is hereby corrected as shown below:

| Column | Line | |
|---|---|---|
| 5 | 34 | Change "improve" to --improves--. |
| 5 | 44 | After "added" change "in" to --to--. |
| 5 | 47 | Change "each 1000 ml" to --1000 ml each--. |
| 5 | 64 | Change "in" to --to--. |
| 6 | 41 | Change "in" to --to--. |
| 6 | 59 | Change "in" to --to--. |
| 6 | 67 | Change "5-I" to --5-1--. |
| 7 | 14 | Change "in" to --to--. |
| 7 | 34 | Change "in" to --to--. |
| 7 | 52 | Change "in" to --to--. |
| 8 | 8 | Change "dimethyl amine" to --dimethylamine--. |

UNITED STATES PATENT AND TRADEMARK OFFICE
CERTIFICATE OF CORRECTION

PATENT NO. : 5,399,700
DATED : 21 March 1995
INVENTOR(S) : Song S. MIN et al.

It is certified that error appears in the above-identified patent and that said Letters Patent is hereby corrected as shown below:

| Column | Line | |
|---|---|---|
| 9 | 2 | Change "in" to --to--. |
| 9 | 11 | Change "were" to --are--. |
| 9 | 38 | Change "being" to --was--. |
| 9 | 43 | Change "on" to --for--. |
| 9 | 45 | Change "were" to --are--. |
| 10 | 2 | Change "on" to --for--. |
| 10 | 4 | Change "were" to --are--. |
| 10 | 36 | Change "were" to --are--. |
| 11 | 7 | Change "were" to --are--. |
| 11 | 22 | Change "in" to --to--. |
| 11 | 31 | Change "were" to --are--. |
| 11 | 51 | Change "were" to --are--. |

UNITED STATES PATENT AND TRADEMARK OFFICE
CERTIFICATE OF CORRECTION

PATENT NO. : 5,399,700
DATED : 21 March 1995
INVENTOR(S) : Song S. MIN et al.

It is certified that error appears in the above-identified patent and that said Letters Patent is hereby corrected as shown below:

| Column | Line | |
|--------|------|---|
| 13 | 45 | Change "followings." to --follows.--. |
| 14 | 33 | Change "water was only" to --only water was--. |
| 14 | 68 | Change "there after" to --thereafter--. |
| 15 | 6 | Change "followings." to --follows.--. |
| 15 | 55 | Change "result" to --results--. |
| 15 | 56 | Change "only Example" to --although Examples--. |

Signed and Sealed this

First Day of April, 1997

BRUCE LEHMAN

*Attest:*

*Attesting Officer*   Commissioner of Patents and Trademarks